United States Patent

Plath et al.

[11] Patent Number: 5,863,864
[45] Date of Patent: Jan. 26, 1999

[54] PREPARATION OF SACCHARINCARBOXYLIC ACIDS AND -CARBOXYLIC ACID ESTERS

[75] Inventors: Peter Plath, Frankenthal; Harald Rang, Altrip; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 776,567

[22] PCT Filed: Jul. 29, 1995

[86] PCT No.: PCT/EP95/03022

§ 371 Date: Feb. 3, 1997

§ 102(e) Date: Feb. 3, 1997

[87] PCT Pub. No.: WO96/05184

PCT Pub. Date: Feb. 22, 1996

[30] Foreign Application Priority Data

Aug. 8, 1994 [DE] Germany .......................... 44 27 996.5

[51] Int. Cl.⁶ .......................... A01N 43/80; C07D 275/06
[52] U.S. Cl. ............................. 504/269; 548/210
[58] Field of Search ............... 548/210; 504/269

[56] References Cited

U.S. PATENT DOCUMENTS

| | | | |
|---|---|---|---|
| 3,673,200 | 6/1972 | Baker et al. | 260/301 |
| 4,410,353 | 10/1983 | Theissen | 71/91 |
| 4,683,233 | 7/1987 | Salzburg et al. | 514/253 |
| 4,889,933 | 12/1989 | Waldner et al. | 546/114 |
| 4,999,426 | 3/1991 | Waldner et al. | 544/127 |
| 5,034,534 | 7/1991 | Milstein | 548/210 |
| 5,160,363 | 11/1992 | Dean | 71/92 |
| 5,236,917 | 8/1993 | Dunlap et al. | 514/233.8 |

FOREIGN PATENT DOCUMENTS

| | | |
|---|---|---|
| 158 074 | 10/1985 | European Pat. Off. . |
| 308 371 | 3/1989 | European Pat. Off. . |
| 323869 | 7/1989 | European Pat. Off. . |
| 483 928 | 5/1992 | European Pat. Off. . |
| 2 525 593 | 10/1993 | France . |
| 671 788 | 1/1939 | Germany . |
| 3607343 | 9/1986 | Germany . |
| 89/10921 | 11/1989 | WIPO . |
| 90/13549 | 11/1990 | WIPO . |

OTHER PUBLICATIONS

Mania et al., Arch. Pharm. (Weinheim) 316, 464–469, 1983.
El–Maghraby et al., Egypt. J. Pharm. Sci., 24(1–4), 105–115, 1983.
Grushin et al., Organometallics, 12, 3846–3850, 1993.
Bumagin et al., J. Organomet. Chem., 358, 563–565, 1988.
Lee et al., Organometallics, 9, 3064–3066, 1990.
*Synthesis of New Arylsulfonylurea Derivatives of Saccharin*, Benicha et al., Aust J. Chem. 1993, 46 903–906.

*Primary Examiner*—Johann Richter
*Assistant Examiner*—Laura R. C. Lutz
*Attorney, Agent, or Firm*—Keil & Weinkauf

[57] ABSTRACT

Saccharincarboxylic acids and -carboxylic acid esters of the formula I

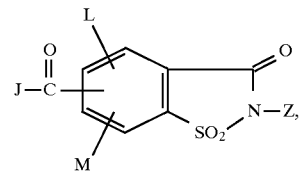

where the substituents have the following meanings:

L and M are hydrogen, alkyl, alkoxy, alkylthio, chlorine, cyano, alkylsulfonyl, nitro or trifluoromethyl;
Z is hydrogen, alkyl, cycloalkyl, alkyl, aryl or aralkyl;
R is H or $C_1$–$C_6$-alkyl, are prepared by reacting corresponding bromo- or iodo-substituted saccharin derivatives of the formula II

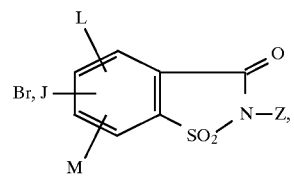

where L, M and Z have the abovementioned meanings, or if Z≠H, compounds of the formula III

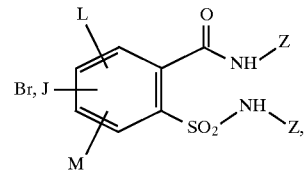

in the presence of a palladium, nickel, cobalt or rhodium transition metal catalyst and of a base with carbon monoxide and water or a $C_1$–$C_6$-alcohol under elevated pressure.

9 Claims, No Drawings

PREPARATION OF SACCHARINCARBOXYLIC ACIDS AND -CARBOXYLIC ACID ESTERS

This application is a 371 of PCT/EP95/03022 filed Jul. 29, 1995.

The present invention relates to the preparation of saccharincarboxylic acids and saccharincarboxylic acid esters of the formula I

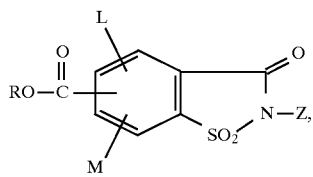

where the substituents have the following meanings:
L and M are hydrogen, alkyl, alkoxy, alkylthio, chlorine, cyano, alkylsulfonyl, nitro or trifluoromethyl;
Z is hydrogen, alkyl, cycloalkyl, aryl or aralkyl;
R is H or $C_1$–$C_6$-alkyl.

The invention further relates to selected saccharin derivatives Ia which have herbicidal activity and serve as intermediates for the preparation of saccharin derivatives in which the OR radical is replaced by other groups. These secondary products are the subject of parallel German applications.

The invention furthermore relates to a method of controlling undesired plant growth using the compounds Ia'.

According to the prior art, eg. DE-A 36 07 343, saccharin derivatives containing a carboxyl substituent in the phenyl ring are obtained via the following reaction sequence:

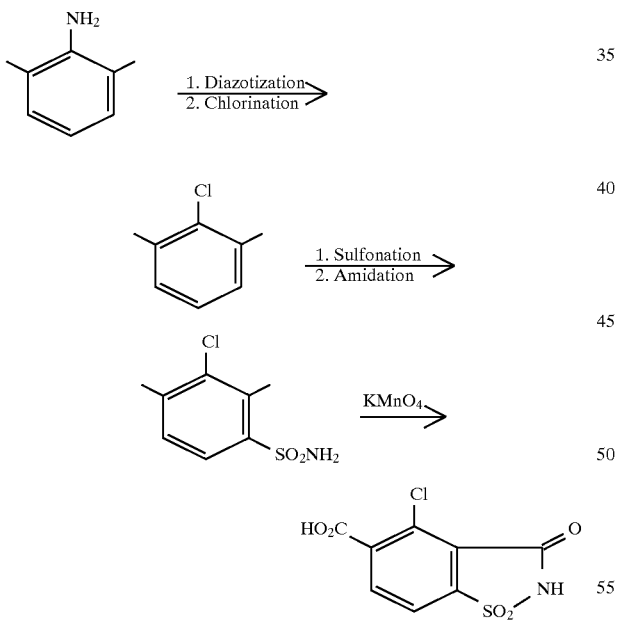

Thus the carboxyl function is introduced into the intermediate by oxidation of a methyl group, oxidative ring closure taking place simultaneously (see also German Reichspatent (DRP) 671 788 from 1936). This method is disadvantageous in that in the presence of a plurality of oxidizable functional groups selective oxidation is not guaranteed. In addition, the number of stages in the entire process is very high, which is inevitably associated with a decrease in yield.

U.S. Pat. No. 5,034,534 describes the preparation of saccharin derivatives by carbonylation of chlorinated aromatic sulfonamides in the presence of complexes of palladium and at least one alkylphosphine ligand. Nothing can be inferred about introduction of the carboxyl function into the phenyl ring of the saccharin structure from this document.

It is an object of the present invention to enable access to saccharin derivatives of the formula I having a carboxyl function in the phenyl ring, in which drastic oxidative methods, such as the use of potassium permanganate, are to be avoided.

We have found that this object is achieved by a process for preparing saccharin derivatives of the formula I, which comprises reacting corresponding bromo- or iodo-substituted saccharin derivatives of the formula II

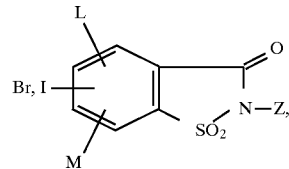

where L, M and Z have the abovementioned meanings, or if Z≠H, compounds of the formula III

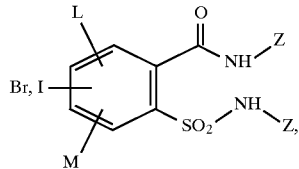

in the presence of a palladium, nickel, cobalt or rhodium transition metal catalyst and of a base with carbon monoxide and water or a $C_1$–$C_6$-alcohol under elevated pressure.

Alkyl radicals in formula I in particular are low-molecular weight alkyl radicals, eg. having 1 to 6 carbon atoms. The same applies for the alkoxy or alkylthio radicals and alkylsulfonyl radicals. Cycloalkyl is eg. $C_3$–$C_8$-cycloalkyl such as cyclopentyl, cyclohexyl or cyclopropyl. Aryl is eg. phenyl which may carry inert substituents. Aralkyl is eg. phenyl-$C_1$–$C_4$-alkyl which may carry inert substituents, such as benzyl or phenethyl.

Reaction equation:

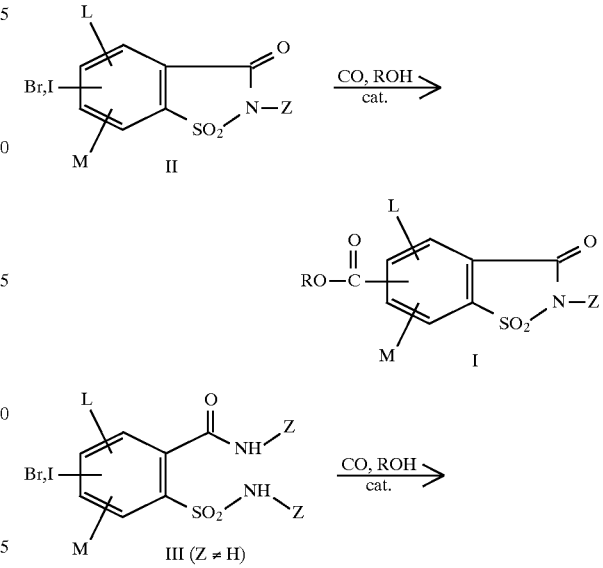

-continued

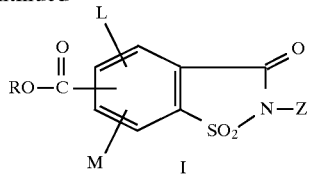

The transition metal-catalyzed conversion of haloaromatics to the corresponding carbonyl or carboxyl compounds by means of carbonylation reagents is known per se, eg. from U.S. Pat. No. 2,640,071; U.S. Pat. No. 3,988,358; U.S. Pat. No. 4,845,273; Urata et al. in J. Org. Chem. 56 (1991), 4320ff; Pri-Bar, Buchman in J. Org. Chem. 53 (1988), 624ff; U.S. Pat. No. 4,990,657, GB-A 2,261,662 and M. Foa et al., J. Organometallic Chem. 285 (1985), 293ff.

The applicability of this method in the case of the specific starting substances II and III is surprising, however. In particular, the success of the process according to the invention had not been expected on the basis of the functional groups present in the starting substances. In addition, it had not been expected that the starting substance III could be converted directly to the carboxylated saccharin derivative I with elimination of the primary amine $ZNH_2$ via the route according to the invention.

The catalysts nickel, cobalt, rhodium and in particular palladium can be present in metallic form or in the form of customary salts, such as in the form of halogen compounds, eg. $PdCl_2$, $RhCl_3.3H_2O$, acetates, eg. $Pd(OAc)_2$, cyanides etc. in the known valency states. Metal complexes with tertiary phosphines, metal alkylcarbonyls, metal carbonyls, eg. $CO_2(CO)_8$, $Ni(CO)_4$, metal carbonyl complexes with tertiary phosphines, eg. $(PPh_3)_2Ni(CO)_2$, or transition metal salts complexed with tertiary phosphines can further be present. The last-mentioned embodiment is particularly preferred in the case of palladium as a catalyst. The nature of the phosphine ligands here is widely variable. For example, they can be represented by the following formulae:

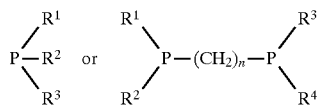

where n is the numbers 1, 2, 3 or 4 and the radicals $R^1$ to $R^4$ are low-molecular weight alkyl, eg. $C_1$–$C_6$-alkyl, aryl or $C_1$–$C_4$-alkylaryl, eg. benzyl, phenethyl or aryloxy. Aryl is eg. naphthyl, anthryl and preferably unsubstituted or substituted phenyl, it only being necessary with respect to the substituents to take into account their inertness to the carboxylation reaction, otherwise they can be widely varied and include all inert C-organic radicals such as $C_1$–$C_6$-alkyl radicals, eg. methyl, carboxyl radicals such as COOH, COOM (M is eg. an alkali metal, alkaline earth metal or ammonium salt), or C-organic radicals bonded via oxygen, such as $C_1$–$C_6$-alkoxy radicals.

The preparation of the phosphine complexes can be carried out in a manner known per se, eg. as described in the documents mentioned at the outset. For example, customary commercially available metal salts such as $PdCl_2$ or $Pd(OCOCH_3)_2$ are used as starting materials and the phosphine, eg. $P(C_6H_5)_3$, $P(n-C_4H_9)_3$, $PCH_3(C_6H_5)_2$ or 1,2-bis(diphenylphosphino)ethane is added. The following catalysts may be mentioned by way of example: 1,3-bis(diisopropylphosphino)propane, tri-p-anisylphosphine, tri-o-tolylphosphine, 1,2-bis(diphenylphosphino)butane, triphenyl phosphite.

The catalyst can also be bound to a polymeric support. The preparation of such catalysts is described, inter alia, in U.S. Pat. No. 5,034,534 or U.S. Pat. No. 4,426,318.

The amount of phosphine, based on the transition metal, is customarily from 0 to 20, in particular from 0.1 to 10, mol equivalents, particularly preferably from 1 to 5 mol equivalents.

The amount of transition metal is not critical. For cost reasons, of course, rather a small amount, eg. from 0.1 to 10 mol %, in particular from 1 to 5 mol %, based on the starting substance II or III, will be used.

Reaction with carbon monoxide and at least equimolar amounts of water, based on the starting substances II or III, is carried out to prepare the saccharincarboxylic acids, ie. R=H. At least equimolar amounts of the appropriate alcohol are advantageously used to prepare the esters, ie. R=$OC_1$–$C_6$-alkyl, eg. $OCH_3$, $OC_2H_5$, O-n-$C_3H_7$, O-i-$C_3H_7$, O-n-$C_4H_9$, O-i-$C_4H_9$, O-tert-$C_4H_9$, O-n-$C_5H_{11}$, O-n-$C_6H_{13}$. The reaction component water or $C_1$–$C_6$-alkyl-OH can simultaneously also be used as a solvent, ie. the maximum amount is not critical.

However, it can also be advantageous, depending on the nature of the starting substances and the catalysts used, to use another inert solvent or the base used for the carboxylation as a solvent instead of the reaction component. In this case, the reaction component water or alcohol is customarily employed in amounts of from 1 to 10, in particular from 1 to 5, mol equivalents, based on II or III.

Suitable inert solvents for carboxylation reactions are customary solvents such as hydrocarbons, eg. toluene, xylene, hexane, pentane, cyclohexane, ethers, eg. methyl tert-butyl ether, tetrahydrofuran, dioxane, dimethoxyethane, substituted amides such as dimethylformamide, persubstituted ureas such as tetra-$C_1$–$C_4$-alkylureas, or nitrites such as benzonitrile or acetonitrile.

In a preferred embodiment of the process, one of the reaction components, in particular the base, is used in an excess such that no additional solvent is necessary.

Bases suitable for the process are all inert bases which are able to bind the hydrogen iodide or hydrogen bromide liberated in the reaction. Examples which can be mentioned here are tertiary amines such as triethylamine, cyclic amines such as N-methylpiperidine or N,N'-dimethylpiperazine, pyridine, amides such as N,N-dimethylformamide, alkali metal or alkaline earth metal hydroxides, carbonates or hydrogen carbonates, and tetraalkyl-substituted urea derivatives such as tetra-$C_1$–$C_4$-alkylurea, eg. tetramethylurea.

The amount of base is not critical, 1 to 10, in particular 1 to 5, mol customarily being used. When the base is simultaneously used as a solvent, as a rule the amount is proportioned such that the reaction components are dissolved, unnecessarily high excesses being avoided for reasons of practicability in order to save costs, to be able to employ small reaction vessels and to guarantee maximum contact of the reaction components.

During the reaction, the carbon monoxide pressure is adjusted such that an excess of CO, based on II or III, is always present. Preferably, the carbon monoxide pressure at room temperature is from 1 to 250 bar, in particular from 5 to 150 bar, of CO.

As a rule, the carbonylation is carried out continuously or batchwise at from 20° to 250° C., in particular at from 30° to 150° C. In the case of batchwise operation, carbon monoxide is expediently injected into the reaction mixture continuously to maintain a constant pressure.

The products can be isolated from the resulting reaction mixture in a customary manner, eg. by distillation.

The starting substances II and III required for the reaction are known or can be prepared in a manner known per se.

They can be obtained either by permanganate oxidation of iodo-substituted 2-methylbenzenesulfonamides or aminosaccharides from Sandmeyer reaction. Aminosaccharins are obtained according to known methods by reduction of nitrosaccharides which, in turn, are either known (Kastle, Amer. Chem. Journal 11 (1889), 184 or DRP 551423 (1930)) or are synthesized from suitable nitrobenzene derivatives (Liebigs Ann. 669 (1963), 85) or benzenesulfonamides in a manner known from the literature.

Moreover, they can be obtained analogously to the preparation procedures of Examples 1 to 12.

The saccharin derivatives I are used for the preparation of crop protection agents, in particular of herbicides of the structure E such as are described in the parallel German Application DE-A 44 27 995.

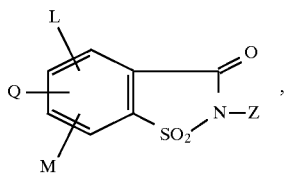

where the substituents have the following meanings:

L and M are hydrogen, $C_1$–$C_4$-alkyl, $C_1$–$C_4$-alkoxy, $C_1$–$C_4$-alkylthio, chlorine, cyano, methylsulfonyl, nitro or trifluoromethyl;

Z is hydrogen, $C_1$–$C_4$-alkyl, $C_3$–$C_8$-cycloalkyl, $C_3$–$C_6$-alkenyl, $C_3$–$C_5$-alkynyl, $C_1$–$C_4$-acyl, or benzyl or phenyl which is unsubstituted or substituted by halogen or $C_1$–$C_4$-alkyl;

Q is a radical CO—J, where

J is a cyclohexane-1,3-dione ring, linked in position 2, of the formula A1

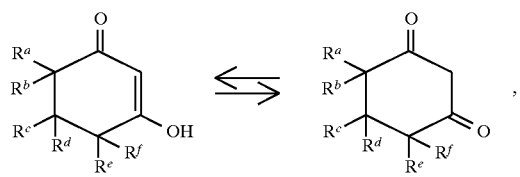

where either $R^a$ to $R^f$ are hydrogen or methyl, or, if $R^a$, $R^b$, $R^c$, $R^e$ and $R^f$ are hydrogen, $R^d$ is 2-ethylthiopropyl, tetrahydropyran-3-yl, tetrahydropyran-4-yl, tetrahydrothiopyran-3-yl or 1-methylthiocyclopropyl, or, if $R^a$, $R^d$, $R^e$ are hydrogen and $R^f$ is methyl, $R^b$ and $R^c$ form a three-membered ring such that a bicyclo[4.1.0] heptane ring of the formula A3 linked in position 2 results.

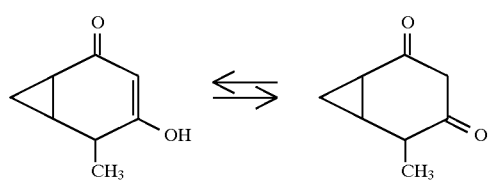

For the preparation of the final products E, the intermediate Ia is converted to the corresponding acid chloride A2

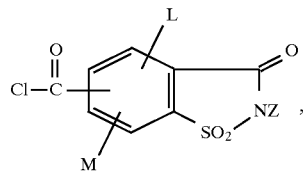

eg. by reaction of the acid (R═H) with thionyl chloride. The starting substance A1 is then acylated with the intermediate A2 and the resulting enol ester is rearranged to the final product E in the presence of a catalyst. This reaction sequence can be represented by the following reaction scheme:

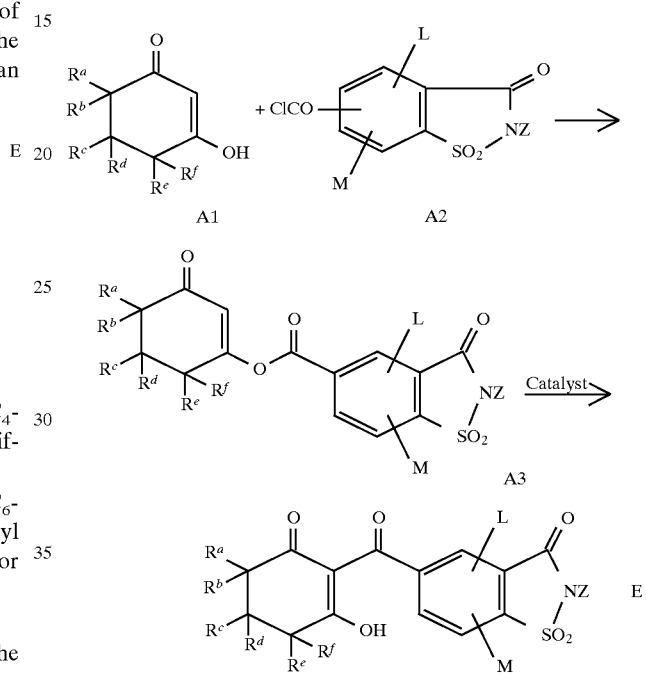

The first step of the reaction sequence, the acylation, is carried out in a generally known manner, eg. by addition of an acid chloride of the formula A2 to the solution or suspension of a cyclohexane-1,3-dione A2 or A3 in the presence of an auxiliary base. The reactants and the auxiliary base are in this case expediently employed in equimolar amounts. Suitable auxiliary bases are tertiary alkylamines, pyridine or alkali metal carbonates, while the solvents used can be methylene chloride, diethyl ether, toluene or ethyl acetate. During the addition of the acid chloride, the reaction mixture is cooled to 0°–10° C., then stirred at 25°–50° C., until the reaction is complete. For working up, the reaction mixture is poured into water and extracted with methylene chloride. After drying the organic phase and removing the solvent, the crude enol ester is employed for the rearrangement without further purification. Preparation examples for benzoyl enol esters of cyclohexane-1,3-diones are found eg. in EP-A 186 118 or U.S. Pat. No. 4,780,127.

The rearrangement of the enol esters to the compounds of the formula E is advantageously carried out at from 20° C. to 40° C. in a solvent and in the presence of an auxiliary base, and with the aid of a cyano compound as a catalyst, the solvent used being acetonitrile, methylene chloride, 1,2-dichloroethane, ethyl acetate or toluene. The preferred solvent is acetonitrile. Suitable auxiliary bases are tertiary alkylamines, pyridine or alkali metal carbonates, which are employed in equimolar amount or an up to four-fold excess.

A preferred auxiliary base is triethylamine in a doubled amount. A suitable catalyst is potassium cyanide or acetone cyanohydrin in an amount of from 1 to 50 mol percent, based on the enol ester. Acetone cyanohydrin is preferably added in an amount of 10 mol percent. Examples of the cyanide-catalyzed rearrangement of enol esters of cyclohexane-1,3-diones are found eg. in EP-A 186 118 or U.S. Pat. No. 4,780,127.

For working up, the reaction mixture is acidified, eg. with dilute mineral acids such as 5% strength hydrochloric acid or sulfuric acid and extracted with methylene chloride or ethyl acetate. For purification, the extract is extracted with cold 5–10% strength alkali metal carbonate solution, the final product passing into the aqueous phase. The product of the formula E is precipitated by acidifying the aqueous solution or extracted again with methylene chloride, dried and then freed from the solvent.

The 1,3-diketones of the formulae A2 and A3 used as a starting material are known or can be prepared by processes known per se (cf. EP-A 71 707, EP-A 142 741, EP-A 243 313, U.S. Pat. No. 4,249,937 and WO 92/13821). Cyclohexane-1,3-dione and dimedone are commercially available compounds.

In a similar manner, saccharin derivatives E can also be prepared in which the cyclohexane-1,3-dione ring is replaced by a pyrazol-4-yl radical. In this case, the starting substances A4 are used

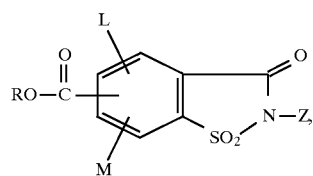

A4 ($R^g$ = H, $CH_3$)

Herbicidally active secondary products of this type are described in the parallel German Application DE-A 44 27 997.

The saccharincarboxylic acids or esters of the formula I not only serve as intermediates for the preparation of herbicidally active secondary products, but themselves have a good herbicidal activity. Accordingly, the use of the compounds Ia' as herbicides or a method for controlling undesired plant growth using the compounds Ia'

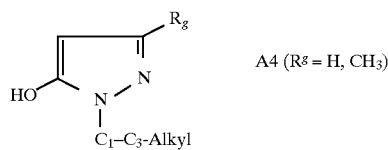

Ia' where the substituents have the following meanings:

L and M are hydrogen, $C_1$–$C_4$-alkyl, $C_1$–$C_4$-alkoxy, $C_1$–$C_4$-alkylthio, chlorine, cyano, methylsulfonyl, nitro or trifluoromethyl;

Z is hydrogen, $C_1$–$C_4$-alkyl, $C_3$–$C_8$-cycloalkyl, benzyl or phenyl, it being possible for the phenyl rings in each case to be unsubstituted or substituted by $C_1$–$C_4$-alkyl, R is H or $C_1$–$C_6$-alkyl, is a further feature of the invention.

The invention moreover relates to novel herbicidally active saccharincarboxylic acids or carboxylic acid esters of the formula Ia

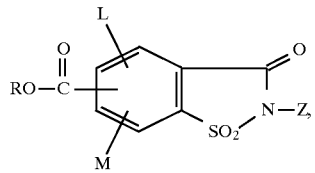

Ia where the substituents have the following meanings:

L and M are hydrogen, $C_1$–$C_4$-alkyl, $C_1$–$C_4$-alkoxy, $C_1$–$C_4$-alkylthio, chlorine, cyano, methylsulfonyl, nitro or trifluoromethyl;

Z is hydrogen, $C_1$–$C_4$-alkyl, $C_3$–$C_8$-cycloalkyl, benzyl or phenyl, it being possible for the phenyl rings in each case to be unsubstituted or substituted by $C_1$–$C_4$-alkyl, R is H or $C_1$–$C_6$-alkyl, with the proviso that Z is not methyl, phenyl, hydrogen or an alkali metal or silver cation if L and M are hydrogen, and further excluding 5-carboxy-7-methylsaccharin and 5-carboxy-4-chlorosaccharin.

Carboxylic acids of the formula Ia (R=H) having one or two further substituents in the phenyl ring, for example having L=$C_1$–$C_4$-alkyl, eg. methyl, chlorine, methylthio, methylsulfonyl or $C_1$–$C_4$-alkoxy such as methoxy and M=hydrogen or $C_1$–$C_4$-alkyl or alkoxy, eg. methyl or methoxy, are particularly preferred.

The compounds Ia or Ia' can be present in the form of their agriculturally utilizable salts, the nature of the salt in general not mattering. Customarily, the salts of those bases are suitable which do not adversely affect the herbicidal action of I or Ia'.

Suitable salts are particularly those of the alkali metals, preferably the sodium and potassium salts, those of the alkaline earth metals, preferably calcium or magnesium salts, and those of the transition metals, preferably silver, copper, zinc and iron salts, and the ammonium salts which can carry one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl-(2-hydroxyethyl)ammonium salts, the phosphonium salts, the sulfonium salts, preferably tri-($C_1$–$C_4$)-alkylsulfonium salts, and the sulfoxonium salts, preferably tri-($C_1$–$C_4$)-alkylsulfoxonium salts.

The compounds Ia or Ia', the herbicidal compositions containing them and their environmentally tolerable salts of, for example, alkali metals, alkaline earth metals or ammonia and amines or the herbicidal compositions containing them can control broad-leaved weeds and grass weeds highly effectively in crops such as wheat, rice, maize, soybeans and cotton without noticeably damaging the crop plants. This effect occurs especially at low application rates.

Taking into account the versatility of the application methods, the compounds Ia, Ia' or compositions containing them can also be employed in a further number of crop plants for the elimination of undesired plants. Examples of suitable crops are the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare,*

*Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum* (*N. rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera, Zea mays.*

Moreover, the compounds Ia and Ia' can also be employed in crops which have been made largely resistant to the action of Ia or Ia' or other herbicides by breeding and/or by means of genetic engineering methods.

The application of the herbicidal compositions or of the active compounds can be carried out preemergence or postemergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The compounds Ia, Ia' or the herbicidal compositions containing them can be applied by spraying, atomizing, dusting, scattering or watering, for example in the form of directly sprayable aqueous solutions, powders, suspensions, even high-percentage aqueous, oily or other suspensions or dispersions, emulsions, oil dispersions, pastes, dusting compositions, scattering compositions or granules. The application forms depend on the intended uses; if possible they should in each case guarantee the finest dispersion of the active compounds according to the invention.

Suitable inert auxiliaries for the preparation of directly sprayable solutions, emulsions, pastes or oil dispersions are essentially: mineral oil fractions of medium to high boiling point such as kerosene or diesel oil, further coal tar oils and oils of vegetable or animal origin, aliphatic, cyclic and aromatic hydrocarbons, eg. paraffins, tetrahydronaphthalene, alkylated naphthalenes or their derivatives, alkylated benzenes and their derivatives, alcohols such as methanol, ethanol, propanol, butanol and cyclohexanol, ketones such as cyclohexanone, or strongly polar solvents, eg. amines such as N-methylpyrrolidone, or water.

Aqueous application forms can be prepared from emulsion concentrates, suspensions, pastes, wettable powders or water-dispersable granules by addition of water. To prepare emulsions, pastes or oil dispersions, the substances can be homogenized in water, as such or dissolved in an oil or solvent, by means of wetting agents, adhesives, dispersants or emulsifiers. However, concentrates consisting of active substance, wetting agent, adhesive, dispersant or emulsifier and possibly solvent or oil which are suitable for dilution with water can also be prepared.

Suitable surface-active substances are the alkali metal, alkaline earth metal or ammonium salts of aromatic sulfonic acids, eg. lignosulfonic, phenolsulfonic, naphthalene-sulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols as well as of fatty alcohol glycol ethers, condensation products of sulfonated naphthalene and its derivatives with formaldehyde, condensation products of naphthalene or of naphthalenesulfonic acids with phenol and formaldehyde, polyoxyethylene octyl phenol ethers, ethoxylated isooctyl-, octyl- or nonylphenol, alkylphenol or tributylphenylpolyglycol ethers, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, scattering and dusting compositions can be prepared by mixing or joint grinding of the active substances with a solid carrier.

Granules, eg. coated, impregnated and homogeneous granules can be prepared by binding of the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

In general, the formulations contain from 0.01 to 95% by weight, preferably from 0.5 to 90% by weight, of active compound. The active compounds are employed here in a purity of from 90% to 100%, preferably from 95% to 100% (according to NMR spectrum). The compounds I according to the invention can be formulated, for example, as follows:

I. 20 parts by weight of the compound No. 1.002 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 1.002 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 1.002 are dissolved in a mixture which consists of 25 parts by weight of cyclohexanone, 65 parts by weight of a mineral oil fraction of boiling point from 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 1.002 are thoroughly mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and ground in a hammer mill. By finely dispersing the mixture in 20,000 parts by weight of water, a spray mixture is obtained which contains 0.1% by weight of the active compound.

V. 3 parts by weight of the active compound No. 1.002 are mixed with 97 parts by weight of finely divided kaolin. In this way, a dusting composition is obtained which contains 3% by weight of the active compound.

VI. 20 parts by weight of the active compound No. 1.002 are intimately mixed with 2 parts by weight of the calcium salt of dodecylbenzenesulfonic acid, 8 parts by weight of fatty alcohol polyglycol ether, 2 parts by weight of the sodium salt of a phenol-urea-formaldehyde condensate and 68 parts by weight of a paraffinic mineral oil. A stable oily dispersion is obtained.

To widen the spectrum of action and to achieve synergistic effects, the saccharin derivatives Ia or Ia' can be mixed with numerous representatives of other herbicidal or growth-regulating active compound groups and applied jointly. For example, suitable mixture components are diazines, 4H-3, 1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1, 3-dione derivatives which carry eg. a carboxyl or carbimino group in the 2 position, quinolinecarboxylic acid derivatives, imidazolinones, sulfonamides, sulfonylureas, aryloxy- or heteroaryloxyphenoxypropionic acids and their salts, esters and amides and others.

Additionally, it may be useful to apply the compounds Ia or Ia' on their own or together in combination with other herbicides, additionally mixed with further crop protection agents, for example with agents for controlling pests or phytopathogenic fungi and bacteria. Further of interest is the miscibility with mineral salt solutions, which are employed for the elimination of nutrition and trace element deficiencies. Nonphytotoxic oils and oil concentrates can also be added.

Depending on the aim of control, time of year, target plants and stage of growth, the application rates of active compound are from 0.001 to 3.0, preferably from 0.01 to 1.0, kg/ha of active substance (a.s.).

PREPARATION EXAMPLES

A) Preparation of the Starting Substances 1. 2-Methyl-6-acetamidobenzoic acid

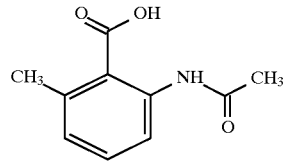

90.6 g (0.6 mol) of 6-methylanthranilic acid are added to a solution of 24.8 g (0.62 mol) of NaOH in 500 ml of water and 63.4 g (0.62 mol) of acetic anhydride are then added dropwise. After stirring for one hour, the mixture is acidified to pH 3 with conc. HCl with cooling, and the precipitate which deposits is filtered off with suction, washed with water and dried under reduced pressure at 50° C. Yield: 107 g (0.55 mol)=92% of theory, m.p.: 189°–190° C.

2. 2-Methyl-3-nitro-6-acetamidobenzoic acid

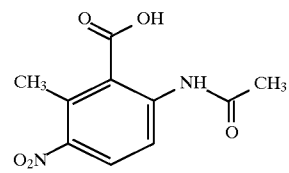

271 ml of 98 percent nitric acid are initially taken at −5° C. and 106 g (0.55 mol) of the 2-methyl-6-acetamidobenzoic acid prepared in 1. are added in portions. After stirring at 10° C. for one hour, the reaction mixture is poured into a mixture of 540 g of ice and 270 ml of water. The deposited precipitate is filtered off with suction, washed with water and dried under reduced pressure at 50° C. Yield: 75.6 g (0.317 mol)=58% of theory, m.p.: 190°–191° C.

The isomer nitrated in the 3 position is deposited from the filtrate after relatively long standing: Yield: 21.3 g (0.089 mol)=16% of theory, m.p.: 180°–182° C.

3. 2-Methyl-3-nitro-6-aminobenzoic acid

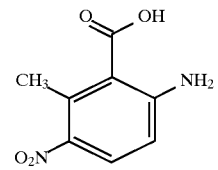

450 ml of 2N NaOH are initially taken and 75.6 g (0.317 mol) of 2-methyl-3-nitro-6-acetamidobenzoic acid are added. The reaction mixture is then warmed to 95° C. and is stirred at this temperature for one hour. After cooling to 10° C., it is acidified by addition of 425 ml of 2N HCl, and the precipitate which deposits is filtered off with suction, washed with water and dried under reduced pressure at 50° C. Yield: 50.7 g (0.258 mol)=82% of theory, m.p.: 183°–184° C.

4. Methyl 2-methyl-3-nitro-6-aminobenzoate

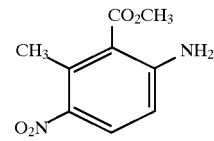

49.7 g (0.253 mol) of 2-methyl-3-nitro-6-aminobenzoic acid are dissolved in 380 ml of acetone and 43 g (0.51 mol) of sodium hydrogen carbonate are added. The mixture is then heated to boiling until evolution of $CO_2$ is complete. 35.3 g (0.28 mol) of dimethyl sulfate are then added dropwise in the course of two hours at the boiling point of acetone to the suspension of the sodium salt of 2-methyl-3-nitro-6-aminobenzoic acid thus obtained, and the mixture is subsequently refluxed for a further three hours and then allowed to cool. After pouring the reaction mixture into 1.8 l of water, it is extracted with methylene chloride. After drying, the organic phase is concentrated. The solid obtained is sufficiently pure for the subsequent reaction (NMR). Yield: 50 g (0.238 mol)=94% of theory, m.p.: 92°–94° C.

5. 2-Methoxycarbonyl-3-methyl-4-nitrobenzenesulfonyl chloride

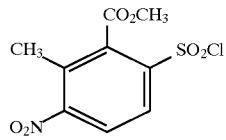

58.5 g (0.278 mol) of methyl 2-methyl-3-nitro-6-aminobenzoate are dissolved with warming in 280 ml of glacial acetic acid and this solution is poured at 15°–20° C. into 85 ml of conc. HCl. A solution of 19.3 g (0.28 mol) of sodium nitrite in 60 ml of water is then added dropwise at 5°–10° C. and the mixture is stirred at 5° C. for 30 min. This diazonium salt solution is subsequently added dropwise to a solution of 374 g of $SO_2$ in 750 ml of glacial acetic acid which contains 14 g of $CuCl_2$ (dissolved in 30 ml of water). After completion of the evolution of nitrogen, the mixture is stirred for a further 15 min and then poured into 1.4 l of ice-water. The sulfonyl chloride is separated off by extraction with 1.2 l of methylene chloride. After drying and concentrating the organic phase, 73 g (0.25 mol) (=90% of theory) of an oil are obtained, which according to NMR (in $CDCl_3$) is pure 2-methoxycarbonyl-3-methyl-4-nitrobenzenesulfonyl chloride.

6. 4-Methyl-5-nitrosaccharin

4-Methyl-5-nitro-1,1,3-trioxo-2,3-dihydro-1$\lambda^6$benz[d]isothiazole (Beilstein nomenclature)

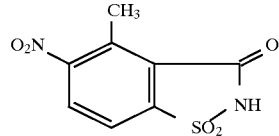

104 ml of 25 percent ammonia solution are initially taken, 100 ml of water are added and a solution of 48.7 g (0.166 mol) of 2-methoxycarbonyl-3-methyl-4-nitrobenzenesulfonyl chloride in 70 ml of tetrahydrofuran is then added dropwise at 10° C. After stirring at 25° C. for three hours, the mixture is concentrated on a rotary evaporator in order to remove water and THF. The residue which remains is stirred with ethyl acetate, filtered off with suction and washed with ethyl acetate. After drying under reduced pressure, 34 g (0.131 mol)=79% of theory of a white solid of m.p.: 312° C. (dec.) are obtained.

7. 2,4-Dimethyl-5-nitrosaccharin

This substance can be prepared by subsequent methylation of the saccharin obtained in 6. using dimethyl sulfate in the presence of NaOH.

8. 3-Methyl-4-nitro-2-(N'-methyl)carboxamido-N-methylbenzenesulfonamide

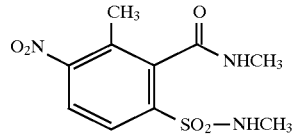

50 ml of water are poured into 50 ml of 40 percent methylamine solution and a solution of 24.3 g (83 mmol) of 2-methoxycarbonyl-3-methyl-4-nitrobenzenesulfonyl chloride in 35 ml of THF is then added dropwise at 10° C. After stirring for one hour at 25° C., all volatile constituents are stripped off on a rotary evaporator, the residue is extracted with ethyl acetate, and the organic phase is washed with water, dried and concentrated. The residue which remains crystallizes after relatively long standing. Yield: 10.3 g (40 mmol=48% of theory), m.p.: 125°–126° C., after recrystallization from ethyl acetate m.p.: 144°–145° C.

9. 4-Methyl-5-amino-1,1,3-trioxo-2,3-dihydro-1$\lambda^6$benz[d]isothiazole (Beilstein nomenclature)

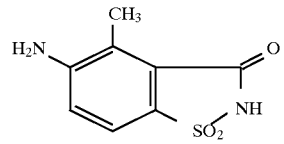

33.6 g (0.13 mol) of 4-methyl-5-nitro-1,1,3-trioxo-2,3-dihydro-1$\lambda^6$benz[d]isothiazole are dissolved in 1.2 l of water with warming to 45° C. and 5 g of Pd/C (10 percent on active carbon) are added. Hydrogen gas is then passed in with vigorous stirring (pressureless hydrogenation). 9 l of $H_2$ are absorbed in the course of 4.5 hours. After cooling to 25° C., the catalyst is filtered off, and the filtrate is concentrated to a volume of 200 ml (on a Rotavapor) and then acidified to pH 1. The deposited precipitate is filtered off with suction, washed with water and dried under reduced pressure at 50° C. 23.4 g (0.11 mol=85% of theory) of a white solid of m.p.: 272°–273° C. are obtained.

10. 4-Methyl-5-iodo-1,1,3-trioxo-2,3-dihydro-1$\lambda^6$benz[d]isothiazole (Beilstein nomenclature)

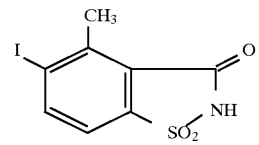

A mixture of 205 ml of glacial acetic acid, 160 ml of water and 40 ml of conc. HCl is initially taken and 23.4 g (0.11 mol) of 4-methyl-5-amino-1,1,3-trioxo-2,3-dihydro-1$\lambda^6$benz[d]isothiazole are introduced with stirring at 15°–20° C. 7.9 g (0.115 mol) of sodium nitrite are added dropwise to the resulting suspension at 5°–10° C. and it is stirred at 5° C. for 30 min. The diazonium salt, which is present as a suspension, is then added dropwise in portions to a solution of 19.1 g (0.115 mol) of potassium iodide in 170 ml of water which is warmed to 50° C., nitrogen being formed. After cooling to room temperature, the deposited product is isolated by filtering off with suction, washed with water and dried under reduced pressure at 50° C. 32.5 g (0.1 mol=91% of theory) of a solid of m.p.: 257°–258° C. are obtained. A combustion analysis gave an iodine content of 38.5% (theory 39.3%).

The product is sufficiently pure for the subsequent reactions.

11. 4-Amino-3-methyl-2-(N'-methyl)carboxamido-N-methylbenzenesulfonamide

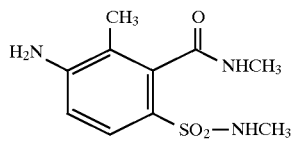

In a similar manner to the procedure described in Example 9, the 3-methyl-4-nitro-2-(N'-methyl)carboxamido-N-methylbenzenesulfonamide obtained according to Example 8 was hydrogenated without pressure. The aniline derivative of abovementioned structure of m.p. 217°–218° C. is obtained in 93% yield.

12. 3-Methyl-4-iodo-2-(N'-methyl)carboxamido-N-methylbenzenesulfonamide

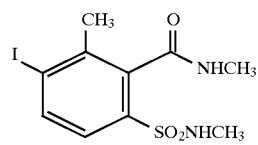

The above compound was diazotized according to the procedure described in Example 10 and converted to the iodobenzene derivative of accompanying structure by reaction with KI. Yield: 95% of theory, m.p.: 60°–62° C.

B) Preparation of the Final Products I

13. 4-Methyl-1,1,3-trioxo-2,3-dihydro-1$\lambda^6$benz[d]isothiazole-5-carboxylic acid

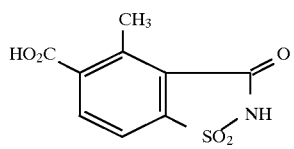

6.4 g (0.02 mol) of 4-methyl-5-iodo-1,1,3-trioxo-2,3-dihydro-1$\lambda^6$benz[d]isothiazole are dissolved in 70 ml of tetramethylurea and 30 ml of water and treated with 0.7 g of bis(triphenylphosphine)palladium dichloride. The mixture is heated to 100° C. in a 300 ml autoclave and stirred at a pressure of 100 bar of carbon monoxide for 36 h.

For working up, the mixture is filtered, and water and tetramethylurea are removed by distillation in a high vacuum. The residue is taken up in methyl tert-butyl ether (MTBE), extracted with NaHCO$_3$ soln. and, after acidifying with HCl, extracted again with MTBE. After concentrating, 2.8 g of 4-methyl-1,1,3-trioxo-2,3-dihydro-1$\lambda^6$benz[d]isothiazole-5-carboxylic acid (58% of theory) are obtained.

$^1$H NMR (DMSO, 400.1 MHz): 2.85 (3H, s); 8.05 (1H, d); 8.2 (1H, d);

$^{13}$C NMR (DMSO, 100.6 MHz): 167.4 (CO); 161.3 (CO); 141.6 (quart. C); 139.7 (quart. C); 138.7 (quart. C); 135.6 (CH); 125.4 (quart. C); 118.5 (CH); 15.4 (CH$_3$).

14. 4-N-Dimethyl-1,1,3-trioxo-2,3-dihydro-1$\lambda^6$benz[d]isothiazole-5-carboxylic acid

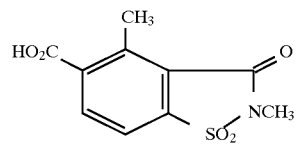

7.3 g (0.02 mol) of 3-methyl-4-iodo-2-(N'-methyl)carboxamido-N-methylbenzenesulfonamide are initially taken in a 300 ml autoclave, together with 0.69 g of bis(triphenylphosphine)palladium dichloride, 30 ml of water and 70 ml of tetramethylurea. The mixture is heated to 100° C. and stirred at a pressure of 100 bar of carbon monoxide for 36 h.

After working up as described in Example 13, 4.1 g of the title compound are obtained (0.014 mol=72% of theory).

$^1$H NMR (DMSO, 400.1 MHz): 2.9 (3H, s); 3.15 (3H, s); 8.2 (2H, 2d); 14.0 (1H, s)

$^{13}$C NMR (DMSO, 100.6 MHz): 167.3 (CO); 158.6 (CO); 139.7 (quart. C); 139.1 (quart. C); 138.9 (quart. C); 135.5 (CH); 124.6 (quart. C); 119.0 (CH); 22.9 (CH$_3$); 15.6 (CH$_3$).

The saccharincarboxylic acids compiled in Table 1 can be obtained in a similar manner. The groups mentioned for a substituent in Table 1 are additionally considered per se, independently of the specific combination with other substituents in which they are mentioned, to be a particularly preferred definition of the substituent concerned.

TABLE 1

| No. | L | M | Z |
|---|---|---|---|
| 1.001 | CH$_3$ | H | H |
| 1.002 | CH$_3$ | H | CH$_3$ |
| 1.003 | CH$_3$ | H | CH$_3$ |
| 1.004 | Cl | H | CH$_3$ |
| 1.005 | SCH$_3$ | H | H |
| 1.006 | SO$_2$CH$_3$ | CH$_3$ | C$_2$H$_5$ |
| 1.007 | H | H | CH$_3$ |
| 1.008 | H | CH$_3$ | H |
| 1.009 | Cl | OCH$_3$ | H |
| 1.010 | OCH$_3$ | CH$_3$ | CH$_3$ |
| 1.011 | CH$_3$ | CH$_3$ | H |
| 1.012 | Cl | CH$_3$ | CH$_3$ |
| 1.013 | CH$_3$ | H | CH$_2$—C$_6$H$_5$ |
| 1.014 | CH$_3$ | H | C$_6$H$_5$ |

C) Reaction of the Compounds I to Give Herbicidally Active Secondary Products 15. 2,4-Dimethylsaccharin-5-carbonyl chloride

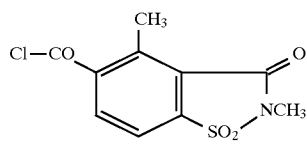

3.8 g (14.9 mmol) of 4,N-dimethyl-1,1,3-trioxo-2,3-dihydro-1$\lambda^6$benz[d]isothiazole-5-carboxylic acid are suspended in 100 ml of toluene, and the mixture is heated to 80° C. and 3.5 g (29.8 mmol) of thionyl chloride are added dropwise. After refluxing for two hours, the solution is decanted hot and the reaction mixture is concentrated on a rotary evaporator. Yield: 74% of theory, m.p.: 149°–150° C.

16. Acylation of Cyclohexanedione

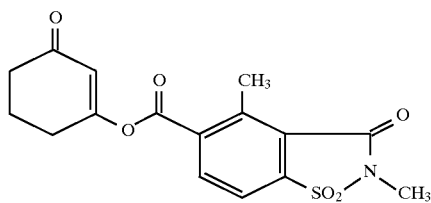

1.21 g (12 mmol) of triethylamine are poured into a suspension of 1.23 g (10.9 mmol) of cyclohexane-1,3-dione in 50 ml of methylene chloride and a solution of 3 g (10.9 mmol) of 4,N-dimethyl-1,1,3-trioxo-2,3-dihydro-1$\lambda^6$benz[d]isothiazole-5-carbonyl chloride in 60 ml of methylene chloride is then added dropwise at 25° C. The mixture is then stirred at 40° C. for 7 hours. After cooling, 60 ml of water are poured in, and the methylene chloride phase is separated off in a separating funnel and dried over magnesium sulfate. The amorphous residue (2.5 g) which remains after stripping off the solvent is the enol ester of accompanying structure, which is rearranged in the next stage without further purification.

17. Rearrangement to the final product E

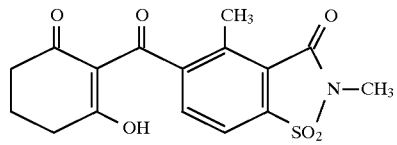

2.5 g (7.2 mmol) of the above enol ester are dissolved in 80 ml of acetonitrile, treated with 3.5 ml of triethylamine and then with 0.33 g (4 mmol) of acetone cyanohydrin and stirred for 16 h. 24.5 g of 5 percent HCl are then added and the reaction mixture is extracted with 100 ml of methylene chloride. The organic phase is then extracted with 5 percent potassium carbonate solution, the product passing into the aqueous phase. By acidifying the alkaline-aqueous solution with conc. HCl, a rubbery solid is precipitated which crystallizes out after rubbing with diisopropyl ether. After washing with petroleum ether, it is dried under reduced pressure. Yield: 0.88 g (35% of theory)

TABLE 2

| No. | $R^a$ to $R^f$ | L | M | Z |
|---|---|---|---|---|
| 2.001 | all H | $CH_3$ | H | H |
| 2.002 | all H | $CH_3$ | H | $CH_3$ |
| 2.003 | $R^c = R^d = CH_3$; $R^a,R^b,R^e,R^f = H$ | $CH_3$ | H | $CH_3$ |
| 2.004 | all H | Cl | H | $CH_3$ |
| 2.005 | all H | $SCH_3$ | H | H |
| 2.006 | all H | $SO_2CH_3$ | $CH_3$ | $C_2H_5$ |
| 2.007 | all H | H | H | $CH_3$ |
| 2.008 | all H | H | $CH_3$ | H |
| 2.009 | $R^c = R^d = CH_3$; $R^a,R^b,R^e,R^f = H$ | Cl | $OCH_3$ | H |
| 2.010 | $R^c = R^d = CH_3$; $R^a,R^bR^e,R^f = H$ | $OCH_3$ | $CH_3$ | $CH_3$ |
| 2.011 | $R^a = CH_3$; $R^b – R^f = H$ | $CH_3$ | $CH_3$ | H |
| 2.012 | $R^c = R^d = CH_3$; $R^a,R^b,R^e,R^f = H$ | Cl | $CH_3$ | $CH_3$ |
| 2.013 | $R^c = R^d = CH_3$; $R^a,R^b,R^e,R^f = H$ | $CH_3$ | H | $CH_2-C_6H_5$ |
| 2.014 | $R^c = R^d = CH_3$; $R^a,R^b,R^e,R^f = H$ | $CH_3$ | H | $C_6H_5$ |

TABLE 3

| No. | J | L | M | Z |
|---|---|---|---|---|
| 3.001 | (bicyclic cyclohexenone with methyl/OH) | $CH_3$ | H | $CH_3$ |
| 3.002 | (cyclohexenone with CH$_3$S-cyclopropyl substituent) | $CH_3$ | H | $CH_3$ |
| 3.003 | (cyclohexenone with CH$_3$S-cyclopropyl substituent) | Cl | Cl | H |

TABLE 3-continued structure: benzene ring with J at one position, L adjacent, C(=O)N(Z)SO2 forming ring, and M substituent

| No. | J | L | M | Z |
|---|---|---|---|---|
| 3.004 | 1-methyl-3-hydroxypyrazol-5-yl-carbonyl | CH$_3$ | H | CH$_3$ |
| 3.005 | 1-methyl-3-hydroxypyrazol-5-yl-carbonyl | SCH$_3$ | H | H |
| 3.006 | 1,4-dimethyl-3-hydroxypyrazol-5-yl-carbonyl | CH$_3$ | H | CH$_3$ |
| 3.007 | 1,4-dimethyl-3-hydroxypyrazol-5-yl-carbonyl | Cl | CH$_3$ | CH$_3$ |
| 3.008 | 1,4-dimethyl-3-hydroxypyrazol-5-yl-carbonyl | CH$_3$ | H | CH$_3$ |

Examples demonstrating the herbicidal effectiveness of compounds Ia and Ia'.

The herbicidal effectiveness of saccharincarboxylic acids or esters of the formulae Ia and Ia' was demonstrated in greenhouse experiments:

The vessels employed were plastic flowerpots filled with sandy loam containing about 3.0% humus. The seeds of the test plants were sown separately, according to species.

TABLE 4 saccharin-type structure with Q, L, M substituents on benzene ring (positions 4,5,6,7) and N–Z

| No. | Q | L | M | Z | M.p. [°C.] |
|---|---|---|---|---|---|
| 4.001 | 4-COO$^{\ominus}$K$^{\oplus}$ | H | H | H | |
| 4.002 | 6-COOCH$_3$ | H | H | NH$_4^{\oplus}$-Salt | 278–280 |
| 4.003 | 6-COOCH$_3$ | H | H | CH$_3$ | 185–187 |
| 4.004 | 4-COOCH$_3$ | H | H | CH$_3$ | 173–174 |
| 4.005 | 6-COOCH$_3$ | H | H | H | >200 |
| 4.006 | 6-COOC$_2$H$_5$ | H | H | CH$_3$ | 123–124 |

TABLE 4-continued

| No. | Q | L | M | Z | M.p. [°C.] |
|---|---|---|---|---|---|
| 4.007 | 5-COOCH$_3$ | H | 6-CH$_3$ | CH$_3$ | 215–216 |
| 4.008 | 6-COOCH$_3$ | H | H | phenyl | 183–185 |

TABLE 5 saccharin-type structure with Q = COOH

| No. | Q position | L | M | Z | M.p. [°C.] |
|---|---|---|---|---|---|
| 5.001 | 5 | 4-CH$_3$ | H | CH$_3$ | 206–207 |
| 5.002 | 6 | H | H | CH$_3$ | >200 |
| 5.003 | 6 | H | H | H | >200 |
| 5.004 | 7 | H | H | CH$_3$ | 227–229 |

Use examples for the herbicidal activity of the compounds Ia and Ia'

It was possible to show the herbicidal action of the saccharincarboxylic acids or esters of the formula Ia and Ia' by greenhouse tests:

The cultivation vessels used were plastic flowerpots containing loamy sand with about 3.0% humus as a substrate. The seeds of the test plants were sown separately according to species.

In the case of preemergence treatment, the active compounds suspended or emulsified in water were applied directly after sowing by means of finely dispersing nozzles. The vessels were lightly watered in order to promote germination and growth, and then covered with transparent plastic hoods until the plants had taken root. This covering causes a uniform germination of the test plants if this was not adversely affected by the active compounds.

For the purpose of postemergence treatment, the test plants were first raised, according to growth form, to a height of growth of from 3 to 15 cm and only then treated with the active compounds suspended or emulsified in water. For this purpose, the test plants were either sown directly and raised in the same vessels or they were first raised separately as seed plants and transplanted into the test vessels a few days before the treatment. The application rate for postemergence treatment was 3.0 kg/ha of a.s.

The plants were kept species-specifically at 10°–25° C. or 20°–35° C. The test period extended over 2 to 4 weeks. During this time, the plants were tended and their reaction to the individual treatments was assessed.

Rating was carried out on a scale of from 0 to 100. 100 in this case means no emergence of the plants or complete destruction of at least the above-ground parts and 0 means no damage or normal course of growth.

The plants used in the greenhouse tests were made up of the following species:

| Botanical name | Common name |
|---|---|
| *Echinocloa crus-galli* | barnyard grass |
| *Setaria italica* | foxtail millet |

At an application rate of 3.0 kg/ha of a.s., undesired plants can be very effectively controlled postemergence using the compound from Example 1.002.

We claim:

1. A process for preparing saccharincarboxylic acids and -carboxylic acid esters of the formula I

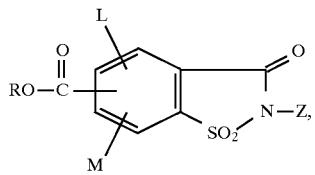

where the substituents have the following meanings:
   L and M are hydrogen, alkyl, alkoxy, alkylthio, chlorine, cyano, alkylsulfonyl, nitro or trifluoromethyl;
   Z is hydrogen, alkyl, cycloalkyl, aryl or aralkyl;
   R is H or $C_1$–$C_6$-alkyl,
which comprises reacting corresponding bromo- or iodo-substituted saccharin derivatives of the formula II

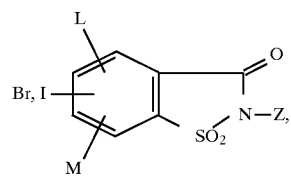

where L, M and Z have the abovementioned meanings, or if Z≠H, compounds of the formula III

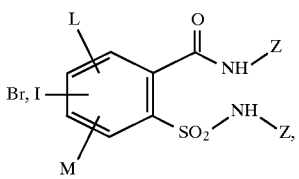

in the presence of a palladium, nickel, cobalt or rhodium transition metal catalyst and of a base with carbon monoxide and water or a $C_1$–$C_6$-alcohol under elevated pressure.

2. A process as claimed in claim 1, wherein palladium catalysts customary for carbonylation reactions are used.

3. A process as claimed in claim 1, wherein the carboxylation is performed in the presence of palladium catalysts which contain phosphine ligands from tertiary phosphines.

4. A process as claimed in claim 1, wherein the base used is a tertiary amine or tetraalkyl-substituted urea derivative.

5. A process as claimed in claim 1, wherein the base used is tetramethylurea.

6. A process as claimed in claim 1, wherein the base is simultaneously used as a solvent.

7. A process as claimed in claim 1, wherein the reaction component water or alcohol is simultaneously used as a solvent.

8. A process as claimed in claim 1, wherein the carboxylation is performed at from 20° to 200° C.

9. A method of controlling undesired plant growth, which comprises applying a herbicidally active amount of a saccharincarboxylic acid or of a -carboxylic acid ester of the formula Ia'

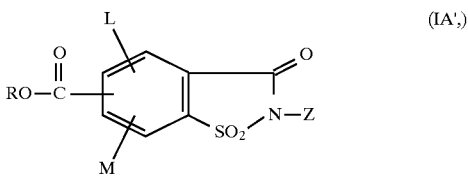

where the substituents have the following meanings:
   L and M are hydrogen, $C_1$–$C_4$-alkyl, $C_1$–$C_4$-alkoxy, $C_1$–$C_4$-alkylthio, chlorine, cyano, methylsulfonyl, nitro or trifluoromethyl;
   Z is hydrogen, $C_1$–$C_4$-alkyl, $C_3$–$C_8$-cycloalkyl, benzyl or phenyl, it being possible for the phenyl rings in each case to be unsubstituted or substituted by $C_1$–$C_4$-alkyl,
   R is H or $C_1$–$C_6$-alkyl,
or an environmentally tolerable salt of the compounds Ia' to plants or their habitat.

* * * * *